United States Patent

Scheibel

[11] 4,091,039
[45] May 23, 1978

[54] HYDROLYSIS OF ETHYLENE GLYCOL ACETATES

[75] Inventor: Edward Scheibel, Media, Pa.

[73] Assignee: Suntech, Inc., Wayne, Pa.

[21] Appl. No.: 791,118

[22] Filed: Apr. 26, 1977

[51] Int. Cl.² .................. C07C 29/00; C07C 27/02; C07C 53/08; C07C 53/22

[52] U.S. Cl. .................. 568/858; 260/540; 260/541; 260/542

[58] Field of Search .......... 260/635 R, 540, 541, 260/542

[56] References Cited

U.S. PATENT DOCUMENTS

| | | | |
|---|---|---|---|
| 1,839,932 | 1/1932 | Ricard et al. | 260/541 |
| 2,033,978 | 3/1936 | Dreyfus | 260/541 |
| 2,859,154 | 11/1958 | Othmer | 260/541 |
| 2,878,283 | 3/1959 | Othmer | 260/541 |
| 3,647,892 | 4/1969 | Hoch | 260/635 R |
| 3,859,368 | 1/1975 | Kollar | 260/635 R |

Primary Examiner—Joseph E. Evans
Attorney, Agent, or Firm—J. Edward Hess; Donald R. Johnson; Paul Lipsitz

[57] ABSTRACT

In the preparation of an alkylene glycol such as ethylene glycol by hydrolysis of the corresponding aliphatic acid ester, the improvement which comprises hydrolyzing the ester in a distillation column, taking to a condenser as overhead a vaporous mixture of water and aliphatic acid from the hydrolysis column, which immiscible stream is mixed with vapors of a water immiscible aliphatic ketone in the condenser, condensing the mixture and conducting the condensate to a settling tank where an upper ketone phase containing extracted aliphatic acid and a lower aqueous phase is formed, recycling the aqueous phase to the hydrolysis column, feeding the ketone phase to a distillation column where the ketone is distilled off and returned to the condenser, and separating essentially anhydrous aliphatic acid from the bottom of the distillation column.

9 Claims, 1 Drawing Figure

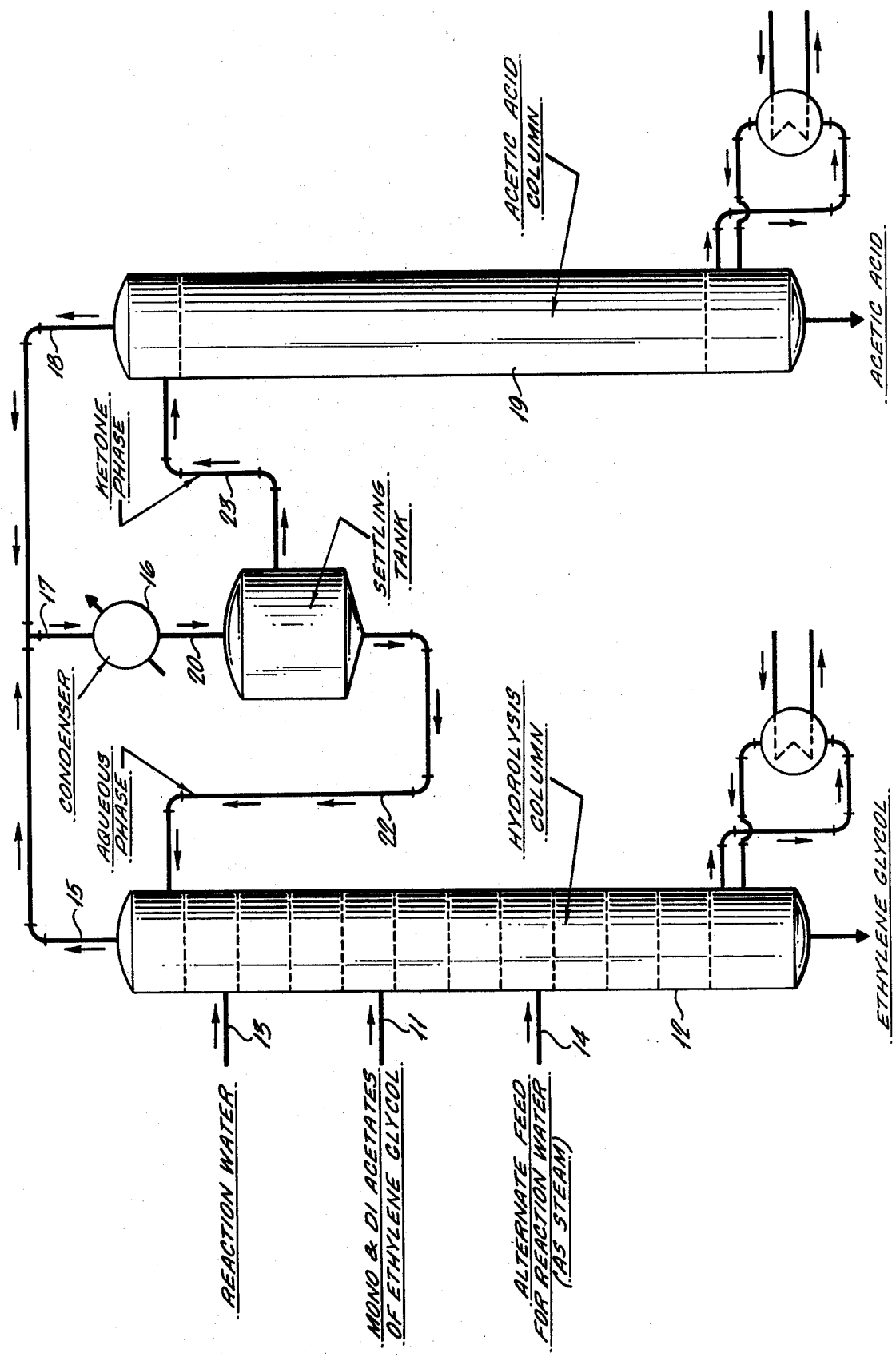

HYDROLYSIS OF ETHYLENE GLYCOL ACETATES

Ethylene glycol may be prepared commerically by either the Halcon process or the Kuraray process wherein direct reaction of ethylene with oxygen in the liquid phase is made to occur using an aliphatic acid such as acetic acid as catalyst. The product glycol produced is in the form of a mixture of its mono- and diacetate esters and these esters must be hydrolyzed to the glycol and the acid is recycled to the catalytic reaction. An excellent discussion of the technology and economics of these processes will be found in Report No. 70 A, Supplement entitled "Ethylene Glycol" by Harold W. Scheeline, October 1975, published by Stanford Research Institue, Menlo Park, California, and this report is hereby incorporated by reference.

In the Halcon process the glycol ester hydrolysis is accomplished by boiling off the acetic acid from an aqueous solution of the esters in a distillation column to yield an aqueous solution of ethylene glycol as a bottoms product. Because of the higher boiling point of acetic acid, a large amount of water must be distilled overhead to remove the acid from the reaction zone. This must subsequently be distilled away from the acetic acid so it can be recycled to the reactor, and, thus consumes a large amount of heat. The bottoms product from the hydrolysis reactor must be separated by fractional distillation, also requiring a large amount of heat.

In the Kuraray process where sulfuric acid is used as catalyst, the acetic acid is removed from the reaction zone by carrying out the hydrolysis of the esters in a liquid extraction column in contact with an isopropyl ether solvent which extracts the acetic acid as it is liberated in the aqueous phase. This enables the reaction to proceed to completion and the ethylene glycol is then separated from the aqueous phase from the bottom of the extractor by distilling off the water. The acid is separated from the light phase in the extraction column by distilling off the solvent for recycle to the hydrolysis reactor, and the acetic acid is returned to the ethylene-oxygen reactor. At atmospheric pressure, the relatively low boiling point of isopropyl ether (69° C) limits the operating temperature of the hydrolysis reactor. Isopropyl ether also tends to form potentially hazardous peroxides under certain operating conditions and such hazards are, of course, undesirable.

It is known from the disclosure of U.S. Pat. No. 3,809,724 that ethylene glycol or 1,2-propylene glycol contained in admixture with lower carboxylic acid esters of the glycol may be recovered by an azeotropic distillation and this azeotropic distillation is integrated with the hydrolysis of the glycol carboxylate esters. As described in the above patent, acetic acid and excess water are distilled off after hydrolysis to leave a residue of the glycol and unconverted glycol esters. The procedure of the patent is then applied to the residue to separate the glycol from the esters. Agents were selected which form lower boiling azeotropes with the glycol than with the esters. This type of azeotroping agent would also form a lower boiling azeotrope with water than with an acid and if used directly in the hydrolysis step they would promote the esterification by preferentially removing the water and returning the acid in the liquid mixture. This type of process is normally used to prepare esters from an alcohol and an acid, (see I.E.C. 37,968 (1945). Suitable azeotroping agents disclosed by U.S. Pat. No. 3,809,724 are those having a boiling point of 135° to 190° C and include certain water immiscible ketones (e.g. 2-octanone). However, by including the azeotroping agent in the hydrolysis medium a problem of separation is encountered which adds to the cost of the process.

It has now been found that the above disadvantages may be obviated and an improved process obtained by carrying out the hydrolysis in a distillation column and extracting the condensed aqueous overhead vapors with a water immiscible aliphatic ketone to recover aliphatic acid.

Reference is now made to the FIGURE to further illustrate the process. The ethylene glycol ester mixture is fed to the hydrolysis column (12) through line 11 and reaction water is fed into an upper portion of the column through line (13) or, alternatively, as steam at a lower portion of the column through line 14. The water for hydrolysis of the acetates may be added to the hydrolysis column as liquid, several trays above the acetate feed; or as steam, several trays below the acetate feed. On the bottom trays of the column the water and acetates are fractionated away from the ethylene glycol and on the upper trays the acetic acid and water are fractionated away from the glycol and the esters. The hydrolysis occurs in the intermediate section of the column, i.e., between the trays where the liquid water and steam would be introduced. The intermediate trays in the hydrolysis column (12) should be designed for appreciable liquid holdup to provide adequate residence time for a close approach to equilibrium concentrations in the hydrolysis reaction. Alternatively, this section of of the column may be packed with an acidic ion exchange resin to catalyze the hydrolysis reaction and reduce the residence time required. The overhead vapors from the column (12) comprising water vapor and acetic acid vapor are taken through lines 15 and 17 to a condenser (16). Also entering the condenser (16) through lines 18 and 17 is an aliphatic ketone extractant, preferably as recovered from the overhead of still 19. The liquid condensate from condenser 16 is fed through line 20 to a settling tank 21 where the liquid ketone containing extracted acid forms an upper layer and water forms a bottom layer. The aqueous phase is withdrawn and passed to the hydrolysis column 12 through line 22 as recycled reaction water. The ketone phase in the settling tank is removed from the settling tank, preferably be decantation, and taken through line 23 to distillation column 19 where the aliphatic acid and ketone are separated by distillation. This column will be operated at a temperature sufficient to distill off the ketone, but below the boiling point of the aliphatic acid (118° C for acetic acid). The ketone overhead is recycled through lines 18 and 17 to the condenser 16 as extractant and the bottoms product of the column is anhydrous aliphatic acid. This acid, or course, may be recycled for reaction with ethylene and oxygen to make the glycol.

Suitable water immiscible aliphatic ketones for this process must boil below 115° C and are exemplified by the lower aliphatic ketones such as methyl ethyl ketone, methyl isopropyl ketone, methyl n-propyl ketone and diethyl ketone. Although methyl ethyl ketone is operable in the process, particularly, if the condensate is at a temperature of about 25° C to about 40° C where the immiscibility of the ketone and water is enhanced, it is not a preferred ketone species.

The azeotroping agents useful in the process of this invention have the ability to remove the acid preferentially from the hydrolysis mixture and return the water to promote further hydrolysis, but are too low boiling to be of any practical use for the separation of glycol from the glycol esters as required in the above discussed U.S. Pat. No. 3,807,724.

The process is applicable to all esters of glycols and will be used preferably with alkylene glycols containing up to about six carbon atoms. However, the process will be operable with any acid moeity. Acids higher boiling than acetic are operable because they form minimum boiling azeotropes with water which facilitates their removal in the overhead product. Formic acid, even though forming a maximum boiling azeotrope with water, is no more difficult to remove from dilute solution with a ketone entrainer than is acetic acid, but in this case the bottom product from the acid will be the formic acid - water maximum boiling azeotrope (22% water) rather than the pure acid. Typical esters of other glycols which may be hydrolyzed by the process include those of propylene, butylene and hexylene glycol, the acid moeity of such glycols being preferably derived from acids of from two to four carbon atoms.

The invention claimed is:

1. In the preparation of an alkylene glycol by hydrolysis of the corresponding aliphatic acid ester, the improvement which comprises hydrolyzing the ester in a distillation column, taking to a condenser as overhead from the hydrolysis column a vaporous mixture of water and aliphatic acid, which overhead stream is mixed with vapors of a water immiscible aliphatic ketone in the condenser, condensing the mixture and conducting the condensate to a settling tank where an upper ketone phase containing extracted aliphatic acid and a lower aqueous phase is formed, recycling the aqueous phase to the hydrolysis column, feeding the ketone phase to a distillation column where the ketone is distilled off and returned to the condenser, and separating essentially anhydrous aliphatic acid from the bottom of the distillation column.

2. In the preparation of ethylene glycol by hydrolysis of the corresponding aliphatic acid esters, the improvement which comprises hydrolyzing the esters in a distillation column, taking to a condenser as overhead from the hydrolysis column a vaporous mixture of water and aliphatic acid, which overhead stream is mixed with vapors of a water immiscible lower aliphatic ketone in the condenser, condensing the mixture and conducting the condensate to a settling tank where an upper ketone phase containing extracted aliphatic acid and a lower aqueous phase is formed, recycling the aqueous phase to the hydrolysis column, feeding the ketone phase to a distillation column where the ketone is distilled off and returned to the condenser, and separating essentially anhydrous aliphatic acid from the bottom of the distillation column.

3. The process of claim 2 where the glycol ester comprises the mono- and diacetates of ethylene glycol.

4. The process of claim 3 where the ketone is methyl ethyl ketone.

5. The process of claim 3 where the ketone is methyl n-propyl ketone.

6. The process of claim 3 where the ketone is methyl isopropyl ketone.

7. The process of claim 3 where the ketone is diethyl ketone.

8. The process of claim 1 where the glycol ester is the formic acid ester of ethylene glycol.

9. The process of claim 1 where the glycol ester is a butyrate ester of ethylene glycol.

* * * * *